US011419755B2

(12) United States Patent
Seo et al.

(10) Patent No.: US 11,419,755 B2
(45) Date of Patent: Aug. 23, 2022

(54) HEATING PATCH, AND WARMING DEVICE FOR SKIN CARE COMPRISING SAME

(71) Applicant: AMOLIFESCIENCE CO., LTD., Seoul (KR)

(72) Inventors: In Yong Seo, Seoul (KR); Song Hee Koo, Gimpo-si (KR); Ji Hyun Lee, Incheon (KR); Seon Ho Jang, Seoul (KR); In Tae Yeo, Seoul (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 379 days.

(21) Appl. No.: 16/614,030

(22) PCT Filed: May 28, 2018

(86) PCT No.: PCT/KR2018/006014
§ 371 (c)(1),
(2) Date: Nov. 15, 2019

(87) PCT Pub. No.: WO2018/221903
PCT Pub. Date: Dec. 6, 2018

(65) Prior Publication Data
US 2020/0078212 A1 Mar. 12, 2020

(30) Foreign Application Priority Data

May 31, 2017 (KR) .......................... 10-2017-0067790
Dec. 12, 2017 (KR) .......................... 10-2017-0169837

(51) Int. Cl.
*A61F 7/00* (2006.01)
*A61F 7/02* (2006.01)

(52) U.S. Cl.
CPC ...... *A61F 7/007* (2013.01); *A61F 2007/0004* (2013.01); *A61F 2007/0052* (2013.01);
(Continued)

(58) Field of Classification Search
CPC ...... A61F 2007/0004; A61F 2007/0052; A61F 7/007; A61F 2007/0071; A61F 2007/0225
See application file for complete search history.

(56) References Cited

U.S. PATENT DOCUMENTS

2010/0038356 A1* 2/2010 Fukuda .................. H01C 7/027
219/549
2011/0172750 A1 7/2011 Cassidy et al.
(Continued)

FOREIGN PATENT DOCUMENTS

JP 10328223 12/1998
KR 20120082880 7/2012
(Continued)

*Primary Examiner* — Kaitlyn E Smith
*Assistant Examiner* — Bradford C. Blaise
(74) *Attorney, Agent, or Firm* — Cantor Colburn LLP

(57) ABSTRACT

Provided is a heating patch. The heating patch includes: a flexible plate-shaped base substrate; an electrode portion including a pair of lead electrodes formed on at least one surface of the base substrate along a longitudinal direction to be spaced apart along a width direction of the base substrate, and a pair of branch electrodes extending from the lead electrodes along the width direction of the base substrate to be not electrically connected to each other and to be overlapped with each other; a heating portion including a conductive heating material disposed in an overlapped part between the branch electrodes which have a predetermined area and face each other to generate heat while conducting the pair of branch electrodes to each other; and a pair of cover members disposed on both sides of the base substrate to prevent the electrode portion and the heating portion from being exposed externally.

17 Claims, 12 Drawing Sheets

(52) U.S. Cl.
CPC ................. *A61F 2007/0071* (2013.01); *A61F 2007/0078* (2013.01); *A61F 2007/0095* (2013.01); *A61F 2007/0225* (2013.01)

(56) References Cited

U.S. PATENT DOCUMENTS

| | | | | |
|---|---|---|---|---|
| 2012/0055918 | A1* | 3/2012 | Yue | H05B 3/34 |
| | | | | 219/552 |
| 2014/0061183 | A1* | 3/2014 | Li | H05B 3/34 |
| | | | | 219/541 |
| 2016/0100977 | A1 | 4/2016 | Lee et al. | |
| 2016/0316520 | A1* | 10/2016 | Feng | H05B 3/84 |

FOREIGN PATENT DOCUMENTS

| | | |
|---|---|---|
| KR | 20130006311 | 11/2013 |
| KR | 20130122948 | 11/2013 |
| KR | 101584039 | 1/2016 |
| KR | 200479645 | 2/2016 |
| KR | 20170004302 | 1/2017 |
| KR | 20170036636 | 4/2017 |
| KR | 20170045726 | 4/2017 |

\* cited by examiner

HEATING PATCH, AND WARMING DEVICE FOR SKIN CARE COMPRISING SAME

CROSS REFERENCE TO RELATED APPLICATIONS

This application is the national phase entry of International Application No. PCT/KR2018/006014, filed on May 28, 2018, which is based upon and claims priority to Korean Patent Application 10-2017-0067790, filed on May 31, 2017 and Korean Patent Application 10-2017-0169837, filed on Dec. 12, 2017. The entire contents of which are incorporated herein by reference

TECHNICAL FIELD

The present invention relates to a heating patch and a skin care warming device including the same.

BACKGROUND ART

Generally, a sheet mask is a product which contains an active material including a variety of ingredients useful for skin such as humectants, a whitening agent, and the like or cosmetics and the like to supply nourishment to skin and to introduce elasticity to skin when the sheet mask is attached to the skin such as a face.

Such sheet masks are manufactured using unwoven fabric and the like such that a large amount of active materials or cosmetics are absorbed into skin. However, effective ingredients included in a sheet mask have had a problem in which it is difficult to obtain a satisfactory skin absorption amount and effect by only using a simple absorption method.

In order to solve this problem, a plurality of methods of improving effective ingredients or compositions of cosmetic material are utilized in conventional sheet masks. However, these methods have problems of increasing manufacturing costs and decreasing efficiency in comparison to the increased costs.

Alternatively, there is provided a method of providing heat through a facial heating body. However, since the conventional method is a shape in which the surface-shaped heating body is simply attached to an outer surface, when the conventional method is applied to a curved part of a body, there is a problem of not being completely in contact with the curved part and there is a limitation in which heat is only generated but heat is not generated at a uniform temperature.

DISCLOSURE

Technical Problem

The present invention is directed to providing a skin care heating patch capable of improving elasticity and pliability and a skin care warming device including the same.

The present invention is also directed to providing a skin care heating patch capable of implementing a uniform heating temperature and a skin care warming device including the same.

Technical Solution

One aspect of the present invention provides a heating patch including a plate-shaped base substrate having flexibility, an electrode portion including a pair of lead electrodes formed on at least one surface of the base substrate along a longitudinal direction and arranged to be spaced apart along a width direction of the base substrate, and a pair of branch electrodes extending from the pair of lead electrodes along the width direction of the base substrate to be not electrically connected to each other and to be overlapped with each other by a predetermined length, a heating portion including a conductive heating material disposed in an overlapped part between the pair of branch electrodes which have a predetermined area and face each other to generate heat simultaneously while conducting the pair of branch electrodes to each other when power is supplied, and a pair of cover members disposed on both sides of the base substrate to prevent the electrode portion and the heating portion from being exposed externally. Here, the heating portion includes a plurality of heating portions arranged to be spaced at predetermined intervals apart along the longitudinal direction of the base substrate, and the plurality of heating portions are formed to have the same resistance.

The heating patch may have a shape in which at least a part includes irregular widths along a longitudinal direction.

A plurality of pairs of branch electrodes may be arranged to be spaced at intervals apart along a longitudinal direction of the base substrate, and a gap between the pair of branch electrodes may be formed to be smaller than a gap between one of the pair of branch electrodes and adjacent one of different pairs of branch electrodes. Here, a gap between the pair of branch electrodes and a side part area of the branch electrodes covered by the conductive heating material may be adjusted such that the plurality of heating portions may have uniform resistance.

The conductive heating material may be a conductive constant-temperature heating material, and the conductive constant-temperature heating material may be phenylthiocarbamide (PTC) material.

Another aspect of the present invention provides a skin care warming device including the two heating patches and a pair of connection cables electrically connected to the two heating patches and each including one end connected to another cable connected to an external power source device.

Another aspect of the present invention provides a skin care warming device including the two heating patches, a pair of connection cables electrically connected to the two heating patches, a connection member which connects the pair of connection cables and has a predetermined length to be worn on user's body, and a battery electrically connected to the pair of connection cables and embedded in the connection member. Here, the battery may be a flexible battery.

Advantageous Effects

According to the present invention, a base substrate may be formed as a nanofiber web having micro air holes and secures flexibility and elasticity so as to be easily attached to a curved attachment part and to increase an adhesive force with the skin.

Also, a plurality of heating portions may generate heat at a uniform temperature so as to reduce a temperature deviation depending on a position. Accordingly, effective ingredients may be evenly absorbed into the skin.

MODES OF THE INVENTION

Figure 1:
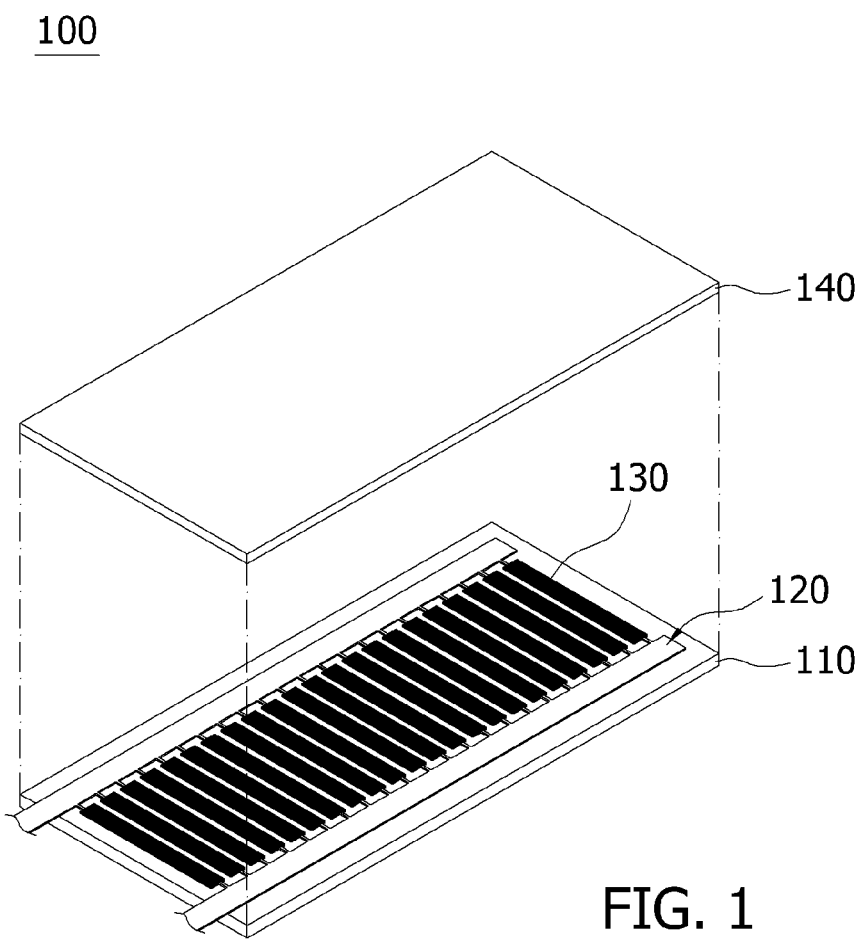
FIG. 1 is a schematic diagram of a heating patch according to one embodiment of the present invention.

Hereinafter, embodiments of the present invention will be described in detail with reference to the attached drawings to allow the embodiments to be easily performed by one of ordinary skill in the art. The present invention may be embodied in a variety of different shapes and is not limited to the embodiments disclosed herein. In order to clearly describe the present invention, parts irrelevant to the present invention are omitted, and the same or similar components are assigned the same reference numerals throughout the drawings.

A heating patch 100 according to one embodiment of the present invention, as shown in FIG. 1, includes a base substrate 110, an electrode portion 120, a heating portion 130, and a cover member 140.

The base substrate 110 may have a plate shape having a predetermined area. The base substrate 110 may support the electrode portions 121 and 122 and the heating portion 130 which are formed on at least one surface thereof. As an example, the base substrate 110 may have approximately the same shape as that of the cover member 140 and may be disposed on one surface of the cover member 140 or disposed therein Here, the base substrate 110 may be formed of material having a flexibility and elasticity. Accordingly, the electrode portion 120 formed on at least one surface of the base substrate 110 may be prevented from being cracked even when the base substrate 110 is deformed by an external force.

For example, the base substrate 110 may be formed of a nanofiber web having micro air holes.

Figure 4:
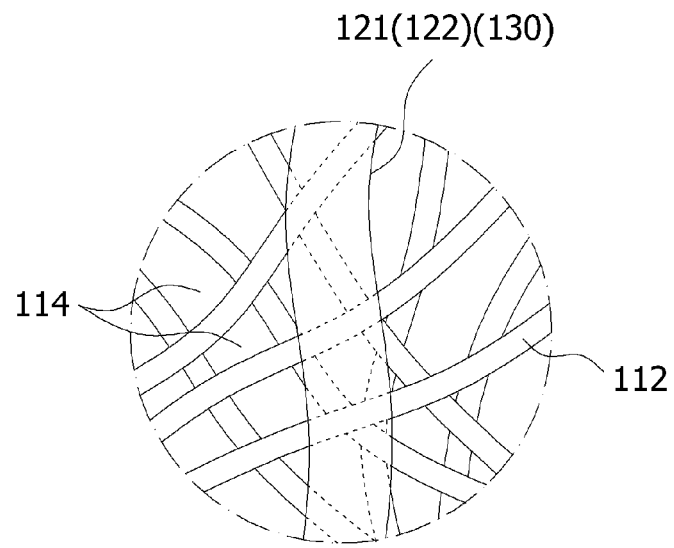
FIG. 4 is a mimetic diagram illustrating a method of forming the electrode portion and the heating portion on the base substrate in the heating patch according to one embodiment of the present invention.

As a detailed example, the base substrate 110 may be a nanofiber web in which nanofibers 112 including synthetic polymers are accumulated in a three-dimensional network structure to have micro air holes 114 as shown in FIG. 4.

Here, in a case in which the electrode portion 120 is formed on one surface of the base substrate 110 using a conductive paste or conductive material, the conductive paste may be filled in the micro air holes 114.

Accordingly, the base substrate 110 may perform a function of a circuit board, on which the electrode portion 120 is formed to be patterned, so as to replace a polyimide film used as a flexible circuit board.

Due to this, the base substrate 110 may have an improved bending property or restoring force in comparison to a conventional flexible circuit board. In other words, the base substrate 110 may have improved flexibility and pliability in comparison to a conventional circuit board and may be restored to an original state through an improved restoring force even when the base substrate 110 is folded or wrinkled.

Also, since the electrode portion 120 is formed by coating and filling a surface of the base substrate 110 and the micro air holes 114 formed in the base substrate 110 with paste particles or particles of a conductive material, an electrode pattern which forms the electrode portion 120 may be barely cracked even when the base substrate 110 is bent or wrinkled.

In addition, since a state is maintained in which at least parts of the electrode portion are connected through the paste filled in the micro air holes 114 even when cracks occur at a part of the electrode pattern which forms the electrode portion 120 due to the base substrate 110 being bent or wrinkled, a possibility of an electrical short-circuit may be significantly reduced.

Here, an opening size of the micro air holes 114 may be formed to have an adequate size in consideration of a particle size of the paste or conductive material. This is because particles of the paste or conductive material may not easily penetrate or impregnate through the micro air holes 114 when the opening size of the micro air holes is too small.

As a detailed example, the base substrate 110 may be a single or multilayer nanofiber web formed by electrically spinning and accumulating a spinning solution, in which synthetic polymers and a solvent are mixed, to have the micro air holes 114. Here, the solvent may be water or alcohol or may be an organic solvent in addition to water or alcohol.

Here, the synthetic polymers may be fibrous-formable polymers having elasticity and flexibility and capable of embodying a nanofiber web through electrospinning. As a non-limited example, the synthetic polymers may be formed using polyvinylidene fluoride (PVDF) separately or may be formed by mixing PVDF with a predetermined amount of polyurethane (PU). However, a material of the synthetic polymers is not limited thereto. A nanofiber web may be implemented through electric spinning, and all well-known materials which are fibrous-formable polymers having elasticity and flexibility may be used.

As described above, since the base substrate 110 for forming the electrode portion 120 is implemented as a nanofiber web using synthetic polymers having flexibility and pliability, the heating patch 100 according to one embodiment of the present invention may secure flexibility and pliability.

Accordingly, in a case in which* the heating patch 100 according to one embodiment of the present invention is attached to a curved attached part, the heating patch 100 may be deformed corresponding to a curved part due to having flexibility and pliability so as to increase an adhesive force with the curved part.

Through this, heat generated by the heating portion 130 may be easily transferred to the attached part. As an example, the curved attached part may be a curved body part of a user such as his or her face.

As described above, the electrode portion 120 may be formed as a predetermined pattern on at least one surface of the base substrate 110 and may provide a path through which a current flows when power is applied.

The electrode portion 120 may be formed as a predetermined pattern on one surface of the base substrate 110 through a variety of well-known methods such as plating, etching, or printing methods using a conductive paste or conductive material.

As a non-limited example, the electrode portion 120 may be formed on the base substrate 110 through a printing method using a conductive paste. The micro air holes 114 formed in the base substrate 110 in addition to the one surface of the base substrate 110 may be completely or partially filled with the conductive paste. Here, the conductive paste may be Ag paste but is not limited thereto, and all well-known conductive pastes used for forming an electrode may be applied.

Here, the electrode portion 120 may include a first electrode portion 121 and a second electrode portion 122 which are not electrically connected to each other, and the first electrode portion 121 and the second electrode portion 122 may be mutually conducted through the heating portion 130 when power is applied.

Figure 2:
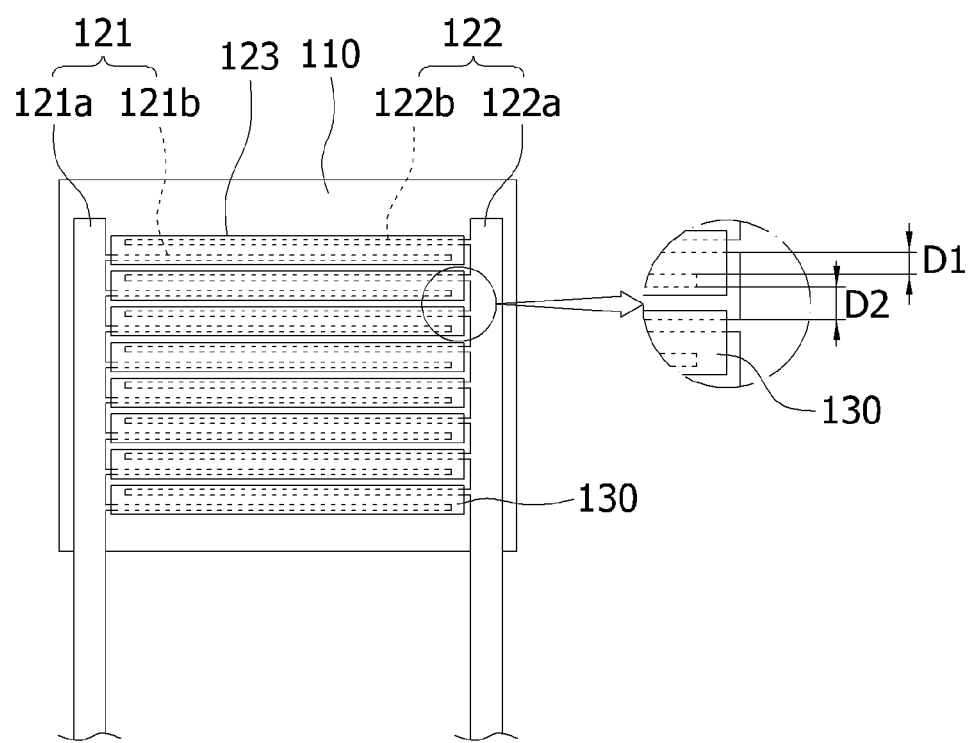
FIG. 2 is a plan view illustrating a state in which an electrode portion and a heating portion, which are applicable to the heating patch according to one embodiment of the present invention are formed on a base substrate.
Figure 3:
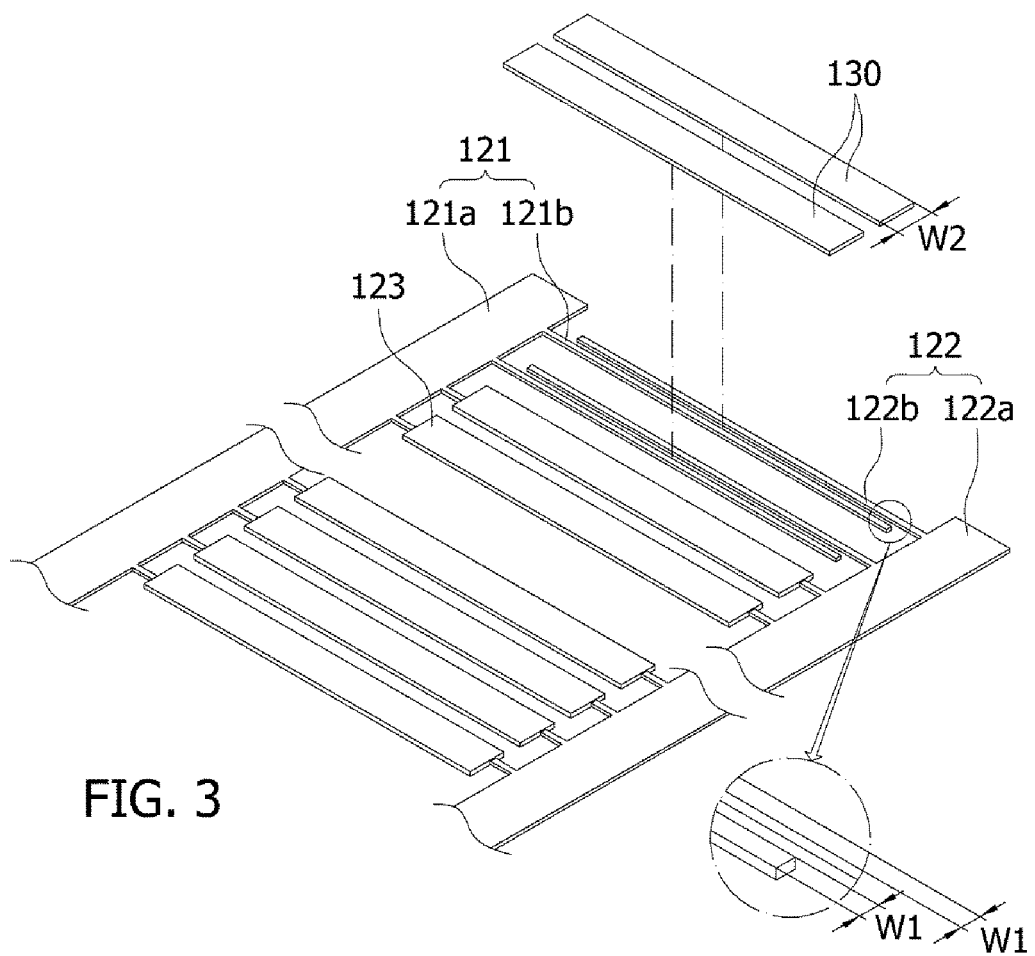
FIG. 3 is a view illustrating an arrangement relationship between the electrode portion and the heating portion which are applicable to the heating patch according to one embodiment of the present invention.

As a detailed example, as shown in FIGS. 2 and 3, the first electrode portion 121 may include a first lead electrode 121a having a predetermined length and a plurality of first branch electrodes 121b extending from the first lead electrode 121a in one direction at predetermined intervals along a longitudinal direction of the first lead electrode 121a.

Also, the second electrode portion 122 may include a second lead electrode 122a having a predetermined length and a plurality of second branch electrodes 122b extending from the second lead electrode 122a in one direction at predetermined intervals along a longitudinal direction of the second lead electrodes 122a.

In the present invention, the first lead electrode 121a and the second lead electrode 122a may be formed along an edge of the base substrate 110, and the first branch electrodes 121b and the second branch electrodes 122b may be formed from the first and second lead electrodes 121a and 122a in a width direction of the base substrate 110.

In addition, the first branch electrodes 121b and the second branch electrodes 122b may be alternately arranged along a longitudinal direction of the base substrate 110, and the first branch electrode 121b and the second branch electrode 122b adjacent to each other may be arranged to be overlapped with each other along at least a part of an entire length thereof.

Accordingly, two first branch electrodes 121b and second branch electrodes 122b arranged to be overlapped by at least a partial length and adjacent to each other may form a pair. A plurality of pairs of the first branch electrodes 121b and the second branch electrodes 122b may be arranged to be spaced at predetermined intervals apart along the longitudinal direction of the base substrate 110.

In this case, the heating portion 130 may be formed to cover an overlapped part between the first branch electrode 121b and the second branch electrode 122b which form a pair. Accordingly, a plurality of such heating portions 130 may be arranged along the longitudinal direction of the base substrate 110 to be spaced apart from each other.

Also, the heating portion 130 may be formed to have an area including a part or an entirety of the overlapped part between the first branch electrode 121b and the second branch electrode 122b which form the pair.

In addition, the heating portion 130 may be formed to have an area including both the overlapped part between the first branch electrode 121b and the second branch electrode 122b which form the pair and widths of the first branch electrode 121b and the second branch electrode 122b which form the pair.

Figure 11:
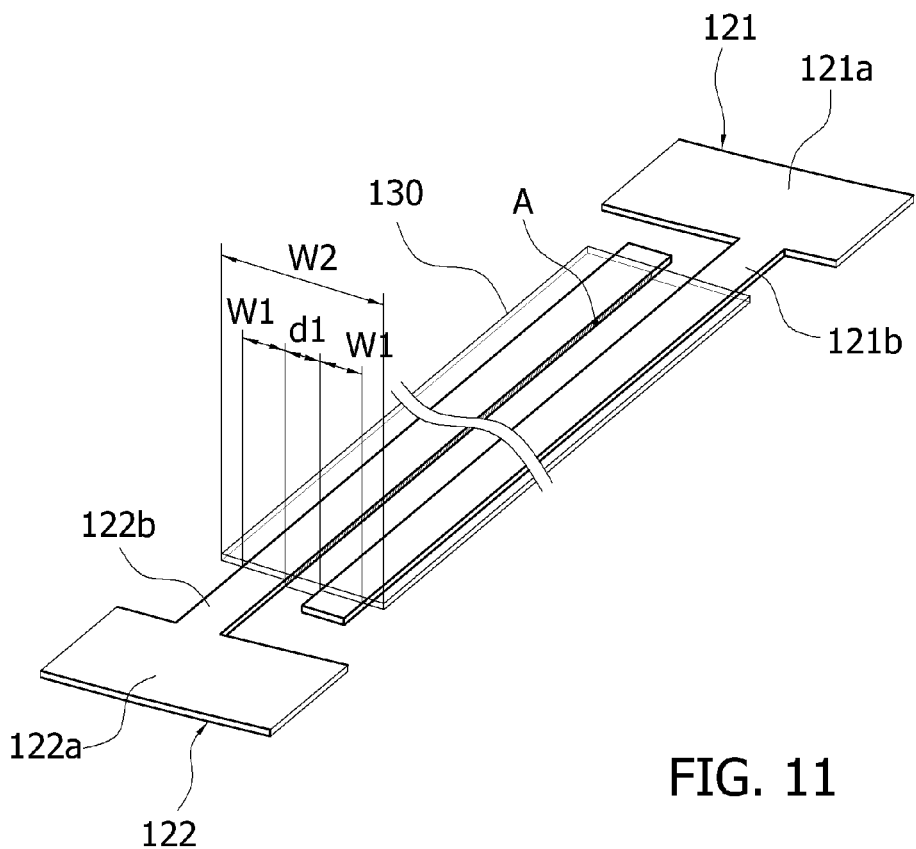
FIG. 11 is a schematic diagram illustrating a state in which a conductive heating material is interposed between a pair of branch electrodes in the heating patch for skin care according to one embodiment of the present invention.

In other words, as shown in FIGS. 2, 3, and 11, a width W2 of the heating portion 130 may be equal to or greater than a size obtained by adding a distance d1 between the first branch electrode 121b and the second branch electrode 122b which form the pair to widths W1 of the first branch electrode 121b and the second branch electrode 122b which form the pair.

Here, the heating portion 130 may be formed of a conductive heating material to conduct the first branch electrode 121b and the second branch electrode 122b which form the pair and to generate heat when power is supplied.

Accordingly, when power is supplied to the electrode portion 120, the first electrode portion 121 and the second electrode portion 122 may be conducted to each other through the heating portion 130 which connects the first branch electrodes 121b to the second branch electrodes 122b, and the heating portion 130 may generate heat using the supplied power.

Through this, since the heating portion 130 generates heat when power is supplied, the heating patch 100 according to one embodiment of the present invention may perform a warming function.

Meanwhile, the heating portion 130 may be formed of a conductive constant-temperature heating material to uniformly generate heat at a target temperature when power is supplied. Here, the conductive constant-temperature heating material may be a material which suppresses a heating temperature by increasing resistance when a temperature increases.

As an example, the conductive constant-temperature heating material may be a well-known phenylthiocarbamide (PTC) material and, in more detail, may be a conductive carbon paste.

Accordingly, in the heating patch 100, when the power is supplied such that a heating temperature of the heating portion 130 increases to a target temperature, the resistance of the heating portion 130 increases such that a current flow may be cut off. Through this, even when the power is continuously supplied, the first electrode portion 121 and the second electrode portion 122 may be prevented from being electrically connected to each other through the heating portion 130.

Also, in the heating patch 100, when the heating temperature of the heating portion 130 is less than the target temperature, the resistance of the heating portion 130 is reduced such that a current flow may be allowed. Through this, the first electrode portion 121 and the second electrode portion 122 may be electrically connected to each other through the heating portion 130 such that a temperature of the heating portion 130 may be increased to the target temperature.

As described above, in the heating patch 100 according to one embodiment of the present invention, the heating portion 130 may generate heat at a uniform temperature at all times by electrically connecting or disconnecting the first electrode portion 121 to or from the second electrode portion 122 through the above-described process.

Meanwhile, the electrode portion 120 may generally be formed of a material including Ag or Cu used for forming an electrode pattern but may be formed of a conductive constant-temperature heating material so that a part or the whole thereof may generate heat when power is applied. Through this, the electrode portion 120 may perform a function of providing heat with the heating portion 130. In this case, the conductive constant-temperature heating material which forms the electrode portion 120 may be formed of the same material as that of the heating portion 130 which has been described above.

Although the first electrode portion 121 and the second electrode portion 122 are formed on the base substrate 110 and then the heating portion 130 is formed as in the drawing, the present invention is not limited thereto, and the heating portion 130 may be formed first on the base substrate 110 and then the first electrode portion 121 and the second electrode portion 122 may be formed on one surface of the heating portion 130.

Here, the heating patch 100 according to one embodiment of the present invention may minimize a difference of temperature generated heat in the plurality of heating portions 130 regardless of an entire shape thereof.

That is, in the heating patch 100, the plurality of heating portions 130 arranged along the longitudinal direction of the base substrate 110 may generate heat at a uniform temperature regardless of forming positions thereof.

Consequently, the heating patch 100 according to one embodiment of the present invention may implement a uniform heating temperature with respect to an entire area thereof.

To this end, the plurality of heating portions 130 arranged along the longitudinal direction of the base substrate 110 may be set to have the same resistance.

That is, the plurality of heating portions 130 may be set to have uniform resistance by adjusting the distance d1 between the first branch electrode 121b and the second branch electrode 122b which form the pair and adjusting side part areas A of the branch electrodes 121b and 122b covered by the conductive heating material.

In the present invention, the side part areas A of the branch electrodes 121b and 122b covered by the conductive heating material may be side part areas formed by protruding thicknesses of the branch electrodes 121b and 122b protruding from one surface of the base substrate 110 or may be side part areas including filling depths of the conductive heating material and conductive paste in the micro air holes 114 in a case in which the micro air holes 114 of the base substrate 110 are filled with the conductive heating material and conductive paste.

Meanwhile, the lead electrodes 121a and 122a may be formed to have relatively greater widths than those of the plurality of branch electrodes 121b and 122b extending from the lead electrodes 121a and 122a.

This is to allow the resistances of the lead electrodes 121a and 122a to have relatively smaller magnitudes than those of the resistances of the branch electrodes 121b and 122b such that power supplied from the outside may be easily transferred toward the branch electrodes 121b and 122b through the lead electrodes 121a and 122a and a heating amount generated by the resistances may be reduced to decrease temperatures of heat generated by the lead electrodes 121a and 122a.

Also, the distance d1 between the first branch electrode 121b and the second branch electrode 122b in which the conductive heating material is disposed may be a relatively smaller distance than a distance d2 between the first branch electrode 121b and the second branch electrode 122b in which the conductive heating material is not disposed. Through this, a temperature of the heating portion 130 may be quickly increased to a target temperature while an amount of the conductive heating material used is minimized.

The cover member 140 may prevent the electrode portion 120 and the heating portions 130 which are formed on at least one surface of the base substrate 110 from being exposed externally. Also, the cover member 140 may prevent a liquid material such as water from flowing into the electrode portion 120 and the heating portion 130.

Accordingly, even when the heating patch 100 according to one embodiment of the present invention is applied to a wet environment, stable driving may be performed by preventing water or the like from flowing into the electrode portion 120 and the heating portion 130 using the cover member 140.

The above-described cover member 140 may cover only the electrode portion 120 and the heating portion 130 locally but may be configured to have an area approximately equal to or broader than that of the base substrate 110 to completely cover the base substrate 110.

To this end, the cover member 140 may have a plate-shaped sheet having a predetermined area to cover the electrode portion 120 and the heating portion 130.

Meanwhile, the cover member 140 may be formed of a material such as a polymer resin such as PU, polyethylene terephthalate (PET), polypropylene (PP), polyethylene (PE), PVDF and the like, release paper, fabric, leather, and the like, may be formed of a silicone material, or may be a molded form covered by a resin material formed of an insulator.

That is, the cover member 140 may be formed of a material having pliability and elasticity like the base substrate 110 having flexibility and pliability and may be formed of a material having a damp-proof property such that the heating patch 100 according to one embodiment of the present invention may be stably used even in the wet environment.

The above cover member 140 may be formed separately on one surface of the base substrate 110 or may be a part of another product such as clothes and the like in a case in which the heating patch 100 according to one embodiment of the present invention is applied to another product such as clothes and the like.

Figure 5:
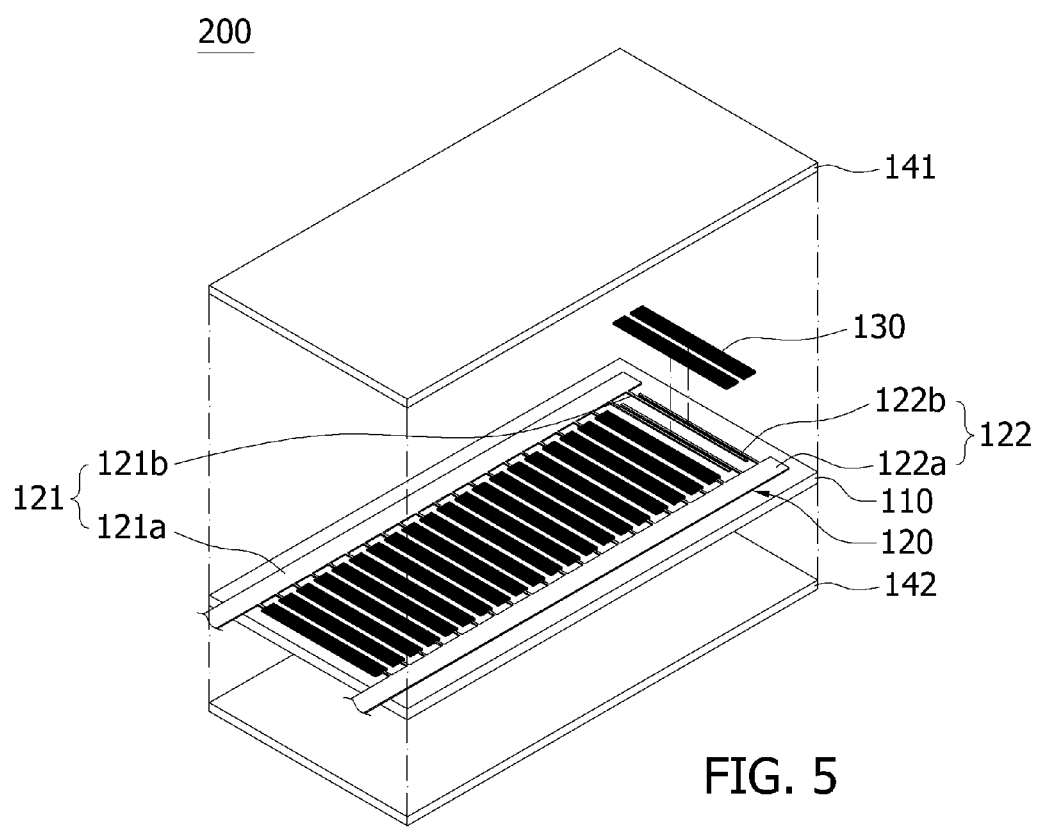
FIG. 5 is a schematic diagram of a heating patch according to another embodiment of the present invention.
Figure 6:
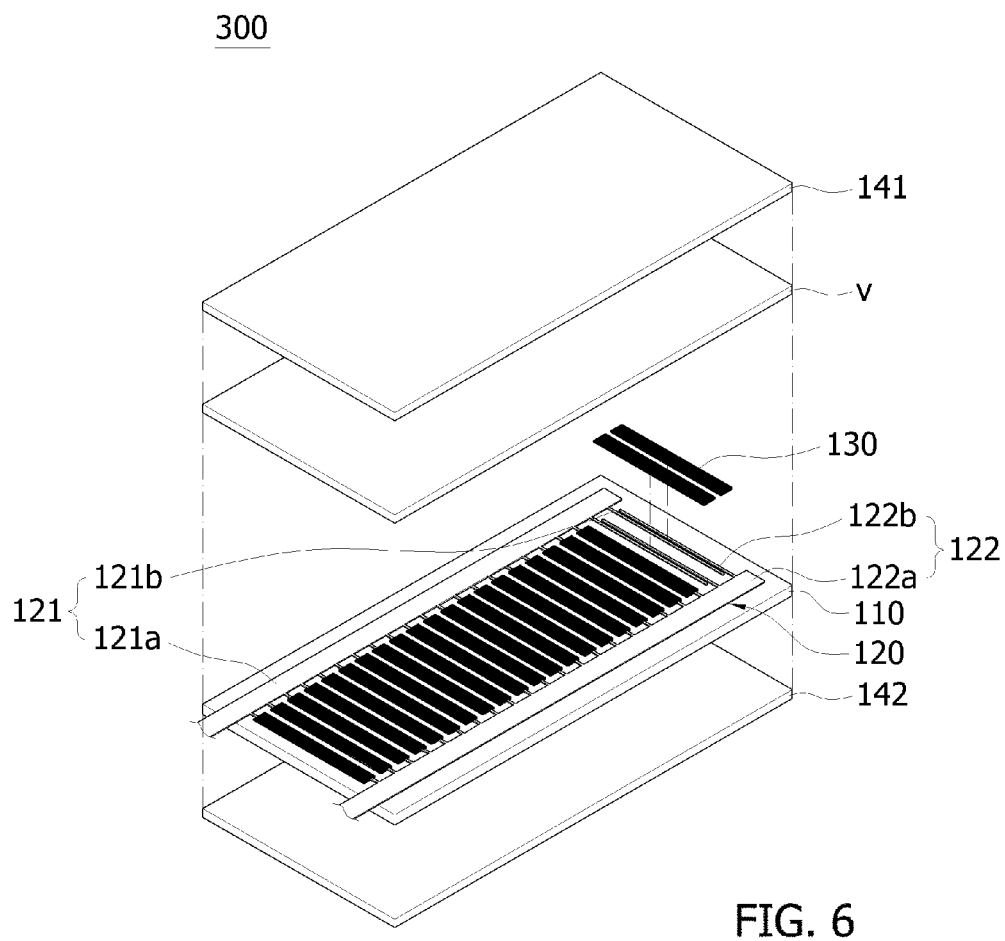
FIG. 6 is a schematic diagram of a heating patch according to still another embodiment of the present invention.

In addition, the cover member 140 may be provided on only the one surface of the base substrate 110 as shown in FIG. 1. Also, as shown in FIGS. 5 and 6, a pair of cover members 141 and 142 may be provided and disposed on both sides of the base substrate 110. Also, in a case in which heating patches 200 or 300 according to one embodiment of the present invention includes the two cover members 141 and 142 disposed on both sides of the base substrate 110, any one of the two cover members 141 and 142 may be a release film which is removed while being used.

Additionally, the cover member 140, 141, or 142 may be attached to one surface of the base member 110 with an adhesive layer as a medium or may be fixed directly to one surface of the base substrate 110 through heat fusing.

Meanwhile, the heating patch 300 according to one embodiment of the present invention may include a thermo-sensitive color-changing material such that a user may easily check a heating temperature of the heating portion 130 which generates heat when power is supplied. Here, the thermo-sensitive color-changing material may be a pigment which is a compound reacting to a temperature and changes color when a set temperature is reached. The thermo-sensitive color-changing material may have a basic color when the set temperature is not reached and have an ivory white when the set temperature is reached.

The thermo-sensitive color-changing material may perform a function of an indicator to check the heating temperature of the heating portion 130 so as to easily check whether the heating temperature increases to a target temperature.

The thermo-sensitive color-changing material may be included in a color-changing layer V disposed between the base substrate 110 and the cover member 141 as shown in FIG. 6. As a detailed example, like the above-described base substrate 110, the color-changing layer V may be a nanofiber web in which nanofibers are accumulated in a three-dimensional network structure through electric spinning of a spinning solution including synthetic polymers and the thermo-sensitive color-changing material.

However, a disposition position of the thermo-sensitive color-changing material is not limited thereto and may be included in an adequate position. As an example, the thermo-sensitive color-changing material may not be included in the color-changing layer V which is separately provided and may be included in the base substrate 110. In this case, the base substrate 110 may be a nanofiber web in which nanofibers are accumulated in the three-dimensional network structure, and the thermo-sensitive color-changing material may be included in a spinning solution for forming the base substrate 110.

Meanwhile, a spinning method for forming the above-described base substrate 110 and/or color-changing layer V may be any one of general electric spinning, air electrospinning, electrospray spinning, electroblown spinning, centrifugal electric spinning, and flash electric spinning.

In addition, the heating patch 100, 200, or 300 according to one embodiment of the present invention may have a variety of shapes and may be implemented as a health-care product, a skin-care product, or the like or may be implemented as a medical product. In addition, it should be noted that the heating patch 100, 200, or 300 according to one embodiment of the present invention may be applied not only to clothing items such as a vest, shoes, clothes, and the like but also to a wearable device such as a smart watch and smart glasses or an aesthetic sheet and the like such as a sheet mask.

Figure 7:
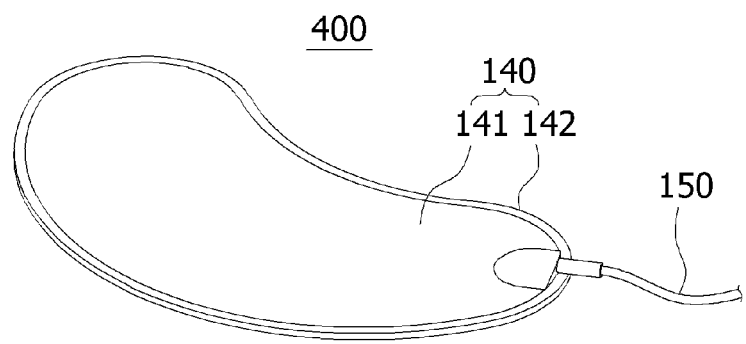
FIG. 7 is a view of a heating patch for skin care according to one embodiment of the present invention.

As a non-limited example, as shown in FIG. 7, the above-described heating patch 100, 200, or 300 may be implemented as a skin care heating patch 400 attached to one surface of a sheet mask or directly attached to a user's skin.

That is, the skin care heating patch 400 may provide heat to a sheet mask or directly provide heat to a user's body so as to provide heat to the user's body.

Accordingly, pores of the user's skin are opened using heat provided from the skin care heating patch 400 such that humectants embedded in the sheet mask or effective ingredients applied to a surface of the skin may penetrate deeply into the skin.

Through this, through heat transferred from the skin care heating patch 400, blood circulation of the user's skin may be improved, penetration of materials useful for skin may be increased by an operation of enlarging a capillary blood vessel, and a skin care effect may be increased and maximized by maximizing an effect of eliminating wastes.

Figure 8:
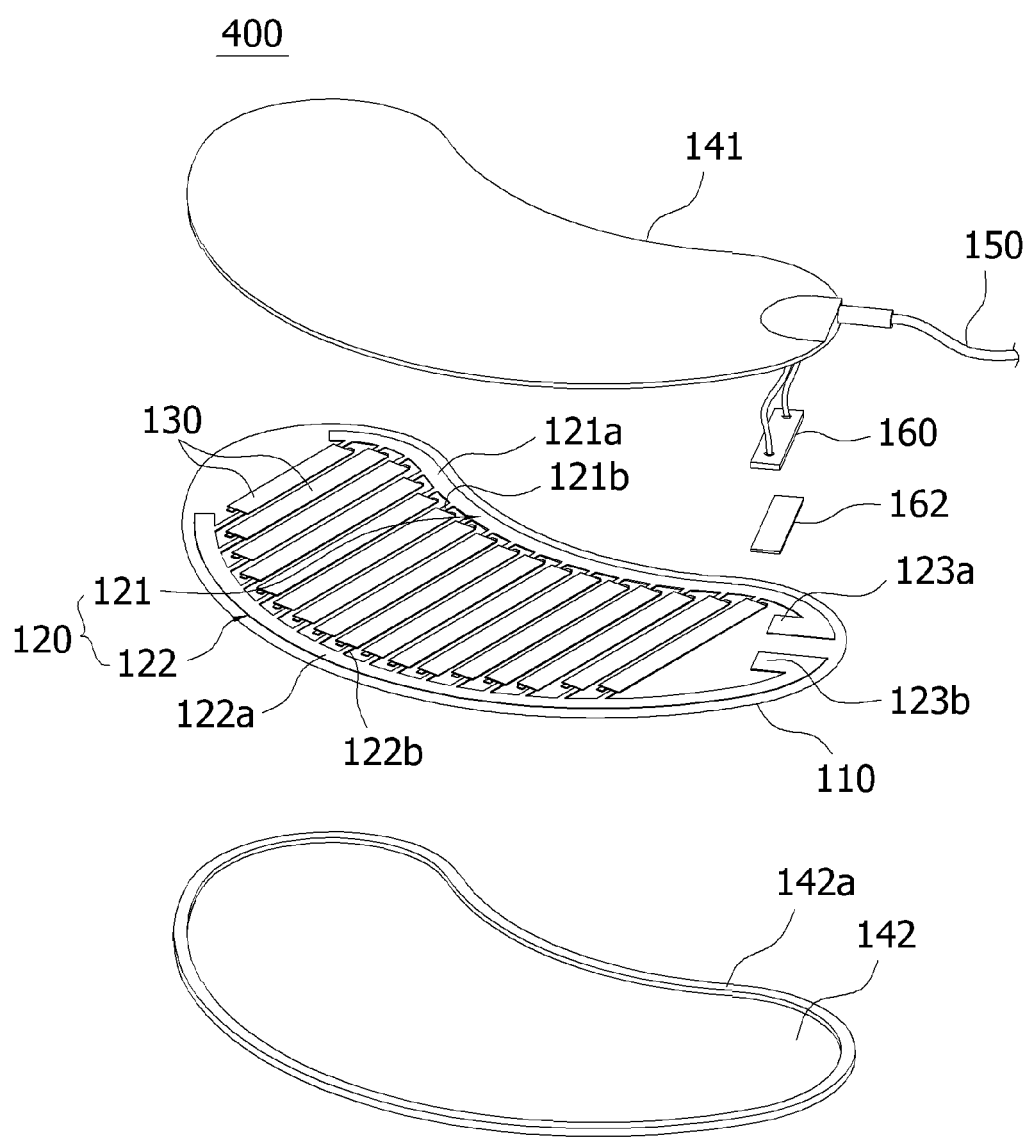
FIG. 8 is an exploded view of FIG. 7.
Figure 9:
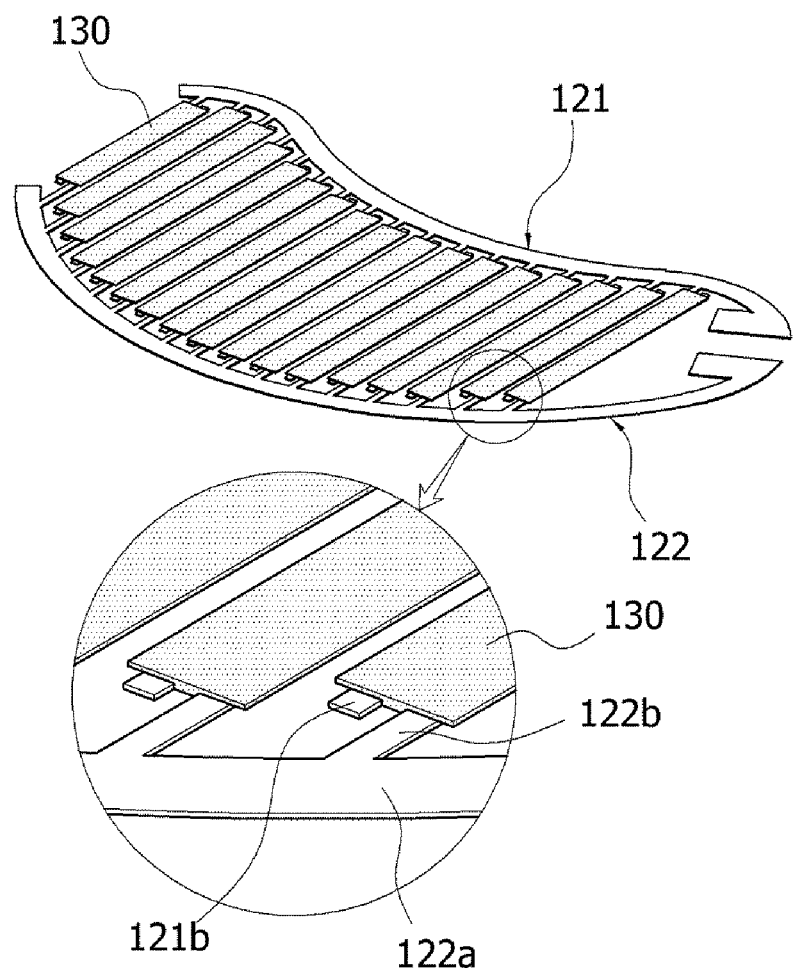
FIG. 9 is a view illustrating an electrode portion and a heating portion which are applicable to the heating patch for skin care according to one embodiment of the present invention.

As a detailed example, the skin care heating patch 400 according to one embodiment of the present invention, as shown in FIGS. 7 and 8, may include the base substrate 110, the electrode portion 120, the heating portion 130, and the cover member 140.

In the embodiment, since the base substrate 110, the electrode portion 120, the heating portion 130, and the cover member 140, which are applied to the heating patch 100, 200, or 300 shown in FIGS. 1 to 6, may be equally applied to the base substrate 110, the electrode portion 120, the heating portion 130, and the cover member 140 and detailed contents are equal to the above description, a detailed description thereof will be omitted.

Meanwhile, the skin care heating patch 400 according to one embodiment of the present invention may have a shape including parts having irregular widths along one direction as shown in FIG. 7.

As an example, the skin care heating patch 400 may have a shape which is a part thereof inwardly concave to one side and may have a shape similar to an eyebrow. Also, the skin care heating patch 400 may have a variety of shapes such as a circular shape excluding a shape having a predetermined width along a longitudinal direction such as a rectangular and a square shape, a circular arc, and a polygonal shape excluding a rectangular shape.

In this case, the base substrate 110 and the cover member 140 may have a shape approximately similar to the shape of the skin care heating patch 400.

However, the shape of the skin care heating patch 400 according to one embodiment of the present invention is not limited thereto and may have a rectangular shape having a uniform width along a longitudinal direction.

Here, the skin care heating patch 400 according to one embodiment of the present invention may be implemented to generate heat at a uniform temperature regardless of a position even though the skin care heating patch 400 has a shape including parts having irregular widths along one direction.

That is, the skin care heating patch 400 according to one embodiment of the present invention may minimize a difference in temperatures of the plurality of heating portions 130 arranged along the longitudinal direction regardless of an entire shape thereof.

Through this, in the skin care heating patch 400 according to one embodiment of the present invention, the plurality of heating portions 130 arranged along a longitudinal direction of the base substrate 110 may generate heat at a uniform temperature regardless of forming positions thereof.

Particularly, even when the skin care heating patch 400 has a shape in which at least a part has different widths along one direction, the plurality of heating portions 130 may generate heat at the same temperature regardless of forming positions thereof. Consequently, the skin care heating patch 400 according to one embodiment of the present invention may implement a uniform heating temperature with respect to an entire area thereof.

To this end, the plurality of heating portions 130 arranged along the longitudinal direction of the base substrate 110 may be set to have the same resistance.

That is, the plurality of heating portions 130 may be set to have uniform resistance by adjusting the distance d1 between the first branch electrode 121b and the second branch electrode 122b which form the pair and adjusting side part areas A of the branch electrodes 121b and 122b covered by the conductive heating material.

In the present invention, the side part areas A of the branch electrodes 121b and 122b covered by the conductive heating material may be side part areas formed by protruding thicknesses of the branch electrodes 121b and 122b protruding from one surface of the base substrate 110 or may be side part areas including filling depths of the conductive heating material and conductive paste in the micro air holes 114 in a case in which the micro air holes 114 of the base substrate 110 are filled with the conductive heating material and conductive paste.

As an example, the plurality of heating portions 130, as shown in FIG. 11, may use a method of adjusting the distance d1 between the first branch electrode 121b and the second branch electrode 122b, which form the pair, on the basis of a part of an overlapped length between the first branch electrode 121b and the second branch electrode 122b, which form the pair, in which the heating portion 130 is formed.

That is, when the overlapped length between the first branch electrode 121b and the second branch electrode 122b, which form the pair, among the plurality of heating portions 130 is relatively great, the distance d1 between the first branch electrode 121b and the second branch electrode 122b, which form the pair, may be relatively great. When the overlapped length between the first branch electrode 121b and the second branch electrode 122b, which form the pair, among the plurality of heating portions 130 is relatively small, the distance d1 between the first branch electrode 121b and the second branch electrode 122b, which form the pair, may be relatively small.

In other words, the distance d1 between the first branch electrode 121b and the second branch electrode 122b, which form the pair, may be formed to have a distance different depending on the overlapped length in which the first branch electrode 121b and the second branch electrode 122b are overlapped.

Through this, in the skin care heating patch 400 according to one embodiment of the present invention, the plurality of heating portions 130 may be set to have the same resistance even when the plurality of heating portions 130 arranged along the longitudinal direction have different lengths. Accordingly, in the skin care heating patch 400, a temperature of heat generated by the heating portions 130 with respect to an entire area may be uniformly maintained regardless of an entire shape.

In addition, since the lengths of the plurality of heating portions 130 may be set to be different from each other, even when the entire shape of the skin care heating patch 400 includes parts having irregular widths along the longitudinal direction, the overlapped length in which the first branch electrode 121b and the second branch electrode 122b, which form the pair, are overlapped may be increased to a part adjacent to the lead electrodes 121a and 122a. Through this, a part generated heat by the heating portions 130 may be extended to an area approximately similar to the entire area of the skin care heating patch 400.

Meanwhile, as shown in FIGS. 8 to 11, the lead electrodes 121a and 122a may be formed to have relatively greater widths than those of the plurality of branch electrodes 121b and 122b extending from the lead electrodes 121a and 122a.

This is to allow the resistances of the lead electrodes 121a and 122a to have relatively smaller magnitudes than those of the resistances of the branch electrodes 121b and 122b such that power supplied from the outside may be easily transferred toward the branch electrodes 121b and 122b through the lead electrodes 121a and 122a and a heating amount generated by the resistances may be reduced to decrease temperatures of heat generated by the lead electrodes 121a and 122a.

Figure 10:
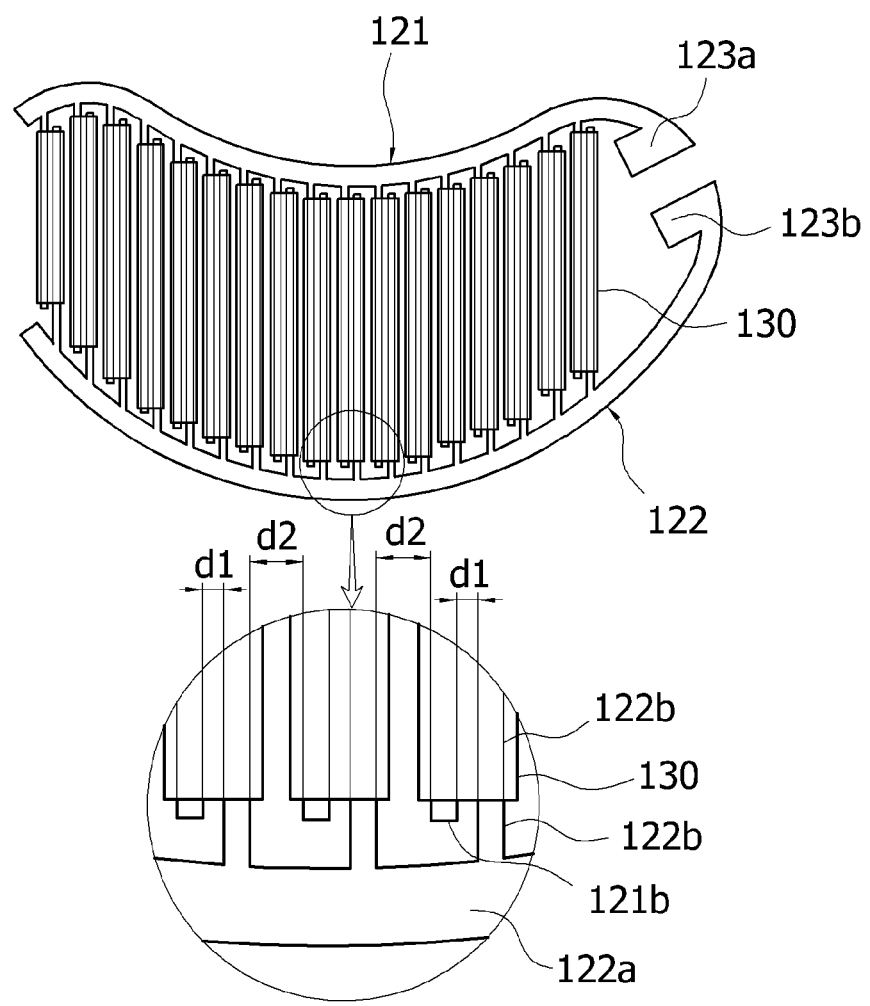
FIG. 10 is a top view illustrating the electrode portion and the heating portion which are applicable to the heating patch for skin care according to one embodiment of the present invention.

Also, as shown in FIG. 10, the distance d1 between the first branch electrode 121b and the second branch electrode 122b in which the conductive heating material is disposed may be a relatively smaller distance that a distance d2 between the first branch electrode 121b and the second branch electrode 122b in which the conductive heating material is not disposed. Through this, a temperature of the heating portion 130 may be quickly increased to a target temperature while an amount of the conductive heating material used is minimized.

The cover member 140 may prevent the electrode portion 121 and 122 and the heating portions 130 which are formed on at least one surface of the base substrate 110 from being exposed externally. Also, even when the skin care heating patch 400 according to one embodiment of the present invention is applied to a wet environment such as a sheet mask or a functional material applied to a user's body, the cover member 140 may prevent a liquid material such as water from flowing into the electrode portions 121 and 122 and the heating portions 130.

Accordingly, even when the skin care heating patch 400 according to one embodiment of the present invention is applied to the wet environment, stable driving may be performed by preventing water or the like from flowing into the electrode portion 121,122 and the heating portion 130 using the cover member 140.

To this end, as shown in FIG. 8, the cover member 140 may include a pair of a first cover member 141 and a second cover member 142 disposed on both sides of the base substrate 110.

Also, the pair of the first cover member 141 and the second cover member 142 may be attached with an adhesive layer as a medium or may be fixed through heat fusing. Here, the adhesive layer may be a liquid or gel phase without a substrate or may be a substrate with adhesive materials applied to both sides thereof.

Here, a protruding portion 142a protruding at a predetermined height along an edge may be formed on one surface of the second cover member 142, and the first cover member 141 and the base substrate 110 may be provided to have an area corresponding to an area of the second cover member 142 excluding the protruding portion 142a.

Accordingly, in a case in which the first cover member 141 and the second cover member 142 are attached with an adhesive layer as a medium, a side end of the first cover member 141 may be in contact with an inner surface of the protruding portion 142a and be surrounded by the protruding portion 142a.

Through this, even when the base substrate 110 disposed inside the cover member 140 has a very small thickness, an edge side of the base substrate 110 may be guided through the protruding portion 142a. Accordingly, the base substrate 110 may be stably mounted on one surface of the cover member 140.

Also, since a gap between the first cover member 141 and the second cover member 142 is formed between the side end of the first cover member 141 and the protruding portion 142a, it is possible to prevent moisture and the like from flowing thereinto through the gap even when one surface of the second cover member 142 comes into contact with the user's skin or one surface of a sheet mask, which contains the moisture and the like.

Meanwhile, the skin care heating patch 400 according to one embodiment of the present invention may further include a cable 150 protruding externally from the cover member 140 to be electrically connected to an external power source.

The cable 150 may include one end electrically connected to each of a pair of connection terminals 123a and 123b formed at end sides of the first electrode portion 121 and the second electrode portion 122 and the other side connected to a well-known connection cable 10. Here, the connection cable 10 may be a charging cable connected to a well-known auxiliary battery.

Through this, in the skin care heating patch 400 according to one embodiment of the present invention, power is supplied from the auxiliary battery to the electrode portions 121 and 122 through the cable 150 connected to the connection cable 10 such that the heating portion 130 may generate heat.

Figure 12:
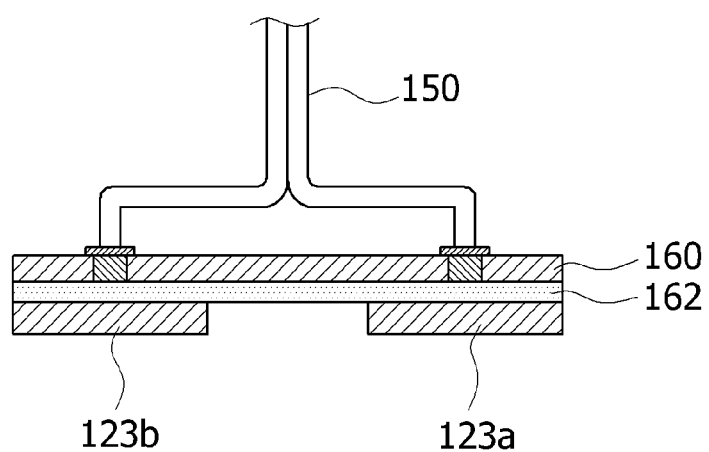
FIG. 12 is a schematic diagram illustrating an electrical connection relation between a cable and the electrode portion in the heating patch for skin care according to one embodiment of the present invention.

To this end, as shown in FIGS. 8 and 12, the cable 150 may be electrically connected to the pair of connection terminals 123a and 123b with a circuit board 160 as a medium. That is, one surface of the circuit board 160 may be attached to the pair of connection terminals 123a and 123b with an adhesive layer 162 as a medium, and the end side of the cable 150 may be bonded to the circuit board 160.

Here, the circuit board 160 may be a printed circuit board (PCB) having an area capable of covering the pair of connection terminals 123a and 123b at the same time, and the adhesive layer 162 may be a well-known anisotropic conductive film.

Accordingly, a local position of the circuit board 160 corresponding to the pair of connection terminals 123a and 123b may be conducted through a via hole and the anisotropic conductive film, and power supplied from the outside through the cable 150 may be supplied to the pair of connection terminals 123a and 123b through the circuit board 160 and the via hole.

Meanwhile, a skin care heating patch 500 according to one embodiment of the present invention may include a cover member 240 with an increased area to increase a contact area with a user's skin while in use.

Figure 13:
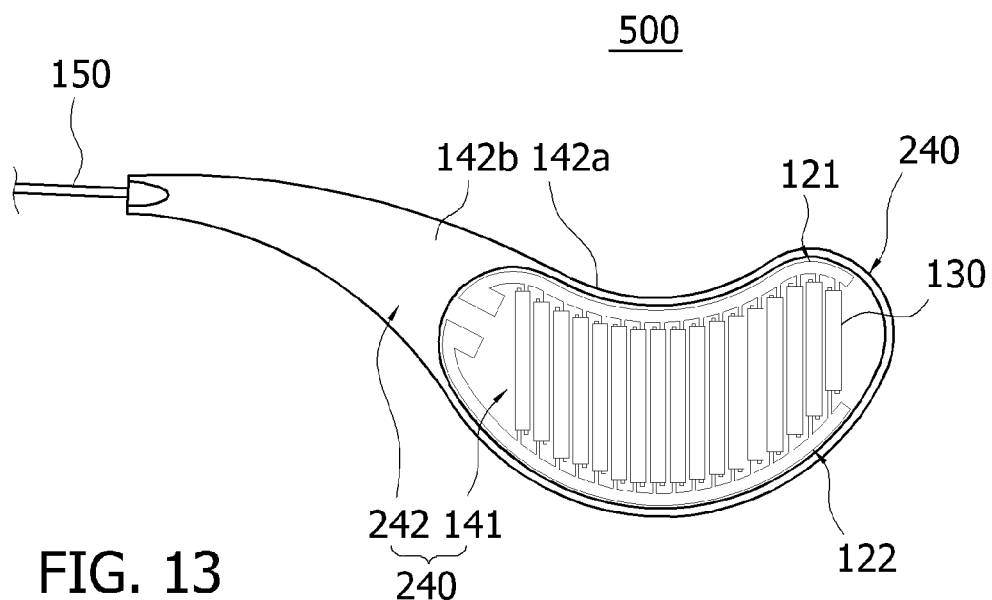
FIG. 13 is a schematic diagram of a heating patch for skin care according to another embodiment of the present invention.

As an example, the cover member 240 may include the first cover member 141 and a second cover member 242. The second cover member 242 may include a first part 242a corresponding to the first cover member 141 and a second part 242b extending with a predetermined area from the first part 242a as shown in FIG. 13.

As described above, the base substrate 110 and the first cover member 141 may be disposed in a region corresponding to the first part 242a, and the second part 242b may come into contact with the user's skin while in use in an area as large as an area corresponding to the second part 242b so as to increase an adhesive force to the user's skin.

In the case of the embodiment, the base substrate 110, the electrode portions 121 and 122, and the heating portion 130 which are equal to those of the above-described embodiment may be arranged between the first cover member 141 and the first part 242a of the second cover member 242. In addition, the cable 150 for electrical connection with an external power source may be employed as the same form as that of the above-described embodiment.

Meanwhile, a skin care heating patch 600 according to one embodiment of the present invention may include a shape in which the base substrate 110, the electrode portions 121 and 122, and the heating portion 130 which have been described above are arranged on both sides of a cover member 340.

Figure 14:
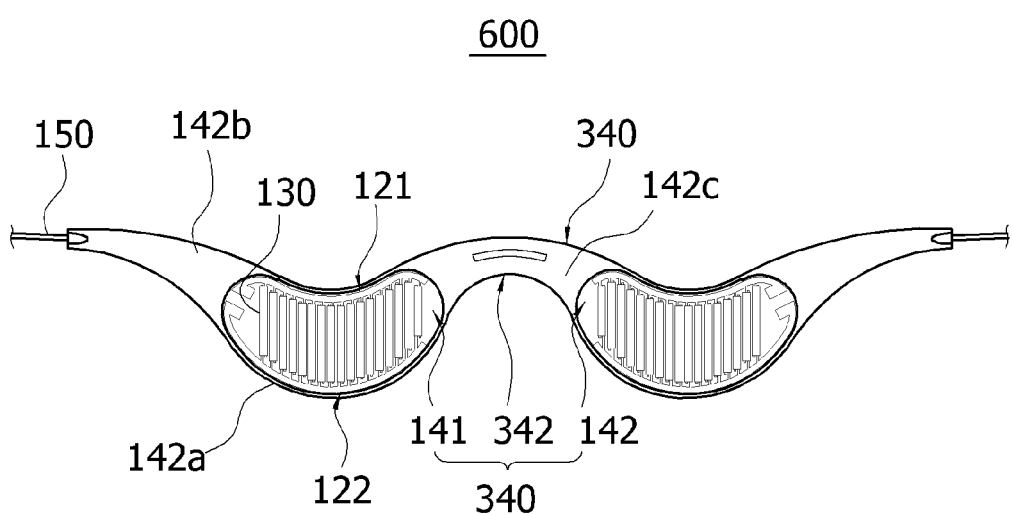
FIG. 14 is a schematic diagram of a heating patch for skin care according to still another embodiment of the present invention.

That is, as shown in FIG. 14, the base substrate 110, the electrode portions 121 and 122, and the heating portion 130 may be arranged on both sides of the cover member 340 on the basis of a virtual boundary line. Through this, heat may be provided to two parts of a user's skin through one skin care heating patch 600 at the same time.

As an example, the skin care heating patch 600 may provide two parts below both eyes of the user with heat at the same time.

To this end, like the above-described embodiment, the cover member 340 may include the first cover member 141 and a second cover member 342. The two first cover members 141 may be provided. The second cover member 342 may include two first parts 342a corresponding to the first cover member 141 and a connecting part 342c which connects the two first parts 342a to each other.

In this case, the second part 342b extending with a predetermined area from the first part 342a may be included on one side of the first part 342a to increase an adhesive force to user's skin.

Also, the base substrate 110 and the first cover member 141 may be disposed in two regions corresponding to the first part 342a, and the second part 342b may come into contact with the user's skin while in use in an area as large as an area corresponding to the second part 342b so as to increase the adhesive force to the user's skin. However, a shape of the second cover member 342 is not limited thereto, and the second part 342b may be omitted.

In the case of the embodiment, the base substrate 110, the electrode portions 121 and 122, and the heating portion 130 which are equal to those of the above-described embodiment may be arranged between the first cover member 141 and the first part 342a of the second cover member 342. In addition, the cable 150 for electrical connection with an external power source may be employed with the same form as that of the above-described embodiment.

Figure 15:
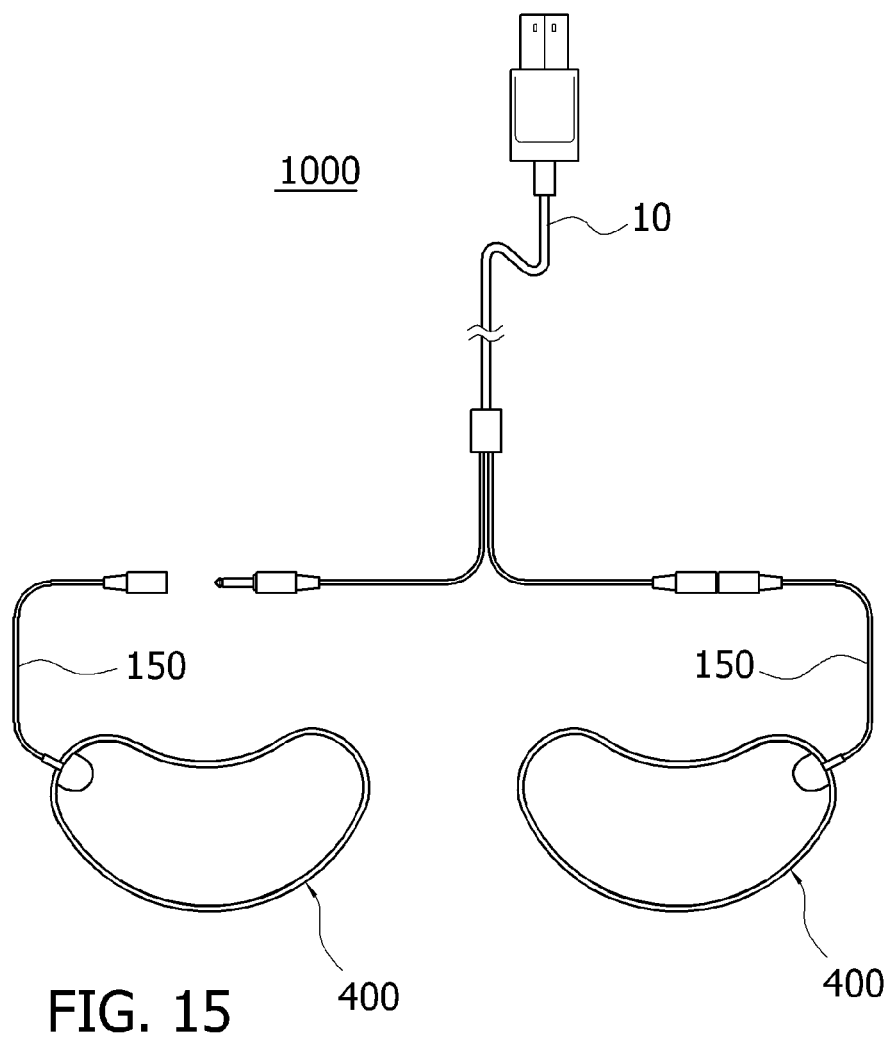
FIG. 15 is a schematic diagram of a skin care warming device according to one embodiment of the present invention.
Figure 16:
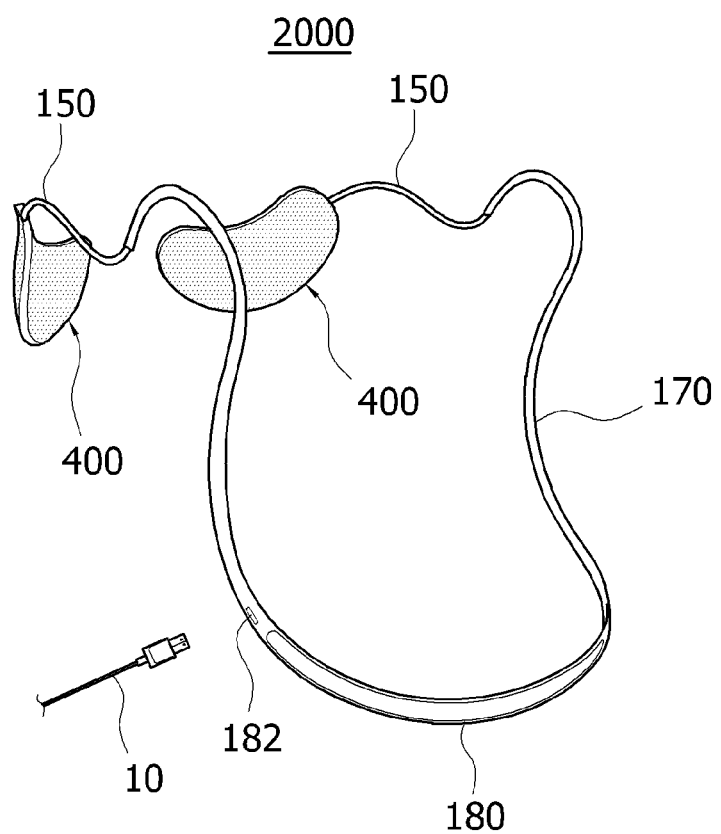
FIG. 16 is a schematic diagram of a skin care warming device according to another embodiment of the present invention.

The above-described skin care heating patch 400, 500, or 600 according to one embodiment of the present invention may be implemented as a skin care warming device 1000 or 2000 for providing user's skin with heat while being worn on a part of the user's body as shown in FIGS. 15 and 16.

Through this, when the skin care heating patch 400 included in the skin care warming device 1000 or 2000 is attached to one surface of a sheet mask, the heating portion 130 included in the skin care heating patch 400 may provide the sheet mask with heat while power is supplied such that the heat may be provided to the user's skin.

Through this, the heat provided to the user's skin may open pores of the user's skin so as to help ingredients embedded in the sheet mask deeply penetrating into the skin. In addition, the heat provided to the skin from the heating portion 130 may improve blood circulation of the user's skin and increase penetration of materials useful for the skin through a capillary expanding action and the like and may increase a skin care effect by maximizing a waste removing effect and the like.

As an example, the skin care warming device 1000 may include, as shown in FIG. 15, the above-described two skin care heating patches 400 and a pair of such connection cables 150 connected to the skin care heating patches 400.

In this embodiment, as the pair of connection cables 150, the above-described cables 150 connected to the electrode portions 121 and 122 of the skin care heating patches 400 may be applied. That is, the pair of connection cables 150 may each include one end electrically connected to each of the pair of connection terminals 123a and 123b formed at end sides of the first electrode portion 121 and the second electrode portion 122 and the other side connected to another cable 10 connected to an external power source device such as a well-known auxiliary battery.

Through this, in the skin care warming device 1000 according to one embodiment of the present invention, power is supplied from the external power source device such as the auxiliary battery through the other cable 10 such that the heating portion 130 may generate heat. In addition, in a case in which the external power source device is a portable auxiliary battery, there is an advantage in which the skin care warming device 1000 may be used without restriction in movement while being possessed or carried. In this case, the skin care warming device 1000 may be worn on a user's body by hanging a middle of a length of the pair of connection cables 150 to the user's ears.

As another example, the skin care warming device 2000 may include, as shown in FIG. 16, the above-described two skin care heating patches 400, the pair of such connection cables 150 connected to the skin care heating patches 400, and a connection member 170.

In this embodiment, as the pair of connection cables 150, the above-described cables 150 connected to the electrode portions 121 and 122 of the skin care heating patches 400 may be applied. That is, the pair of connection cables 150 may each include one end electrically connected to each of the pair of connection terminals 123a and 123b formed at end sides of the first electrode portion 121 and the second electrode portion 122 and a partial or entire length may be embedded in the connection member 170.

Accordingly, the user may wear the device using a method of hanging the device on the user's ears using the connection member 170. In this case, a battery 180 having a predetermined length may be embedded in the connection member 170.

Accordingly, the skin care warming device 2000 according to the embodiment may be driven using power of the battery 180 embedded in the connection member 170 without the need of receiving additional power from the outside so as to increase portability and use convenience.

Here, the battery 180 may be a primary battery or a secondary battery. In addition, as the battery 180, a well-known flexible battery may be employed in order to reduce a total weight and a thickness of the connection member 170 and to be flexible in responding to deformation of the connection member 170 in a case in which the connection member 170 is formed of a deformable material.

In addition, in a case in which the battery 180 is a secondary battery, a charge port 182 for recharging the battery 180 may be formed on one side of the connection member 170. Additionally, although not shown in the drawing, in a case in which the battery 180 is embedded in the connection member 170, a circuit board on which a variety of circuits and semiconductor elements for charging or discharging and controlling overall driving of the battery 180 are mounted may also be embedded in the connection member 170.

Meanwhile, although the skin care warming device 1000 or 2000 is shown in the drawing as being implemented through the skin care heating patch 400 having the shape shown in FIG. 7, the skin care warming device 1000 or 2000 is not limited thereto and may be implemented as a shape to which the skin care heating patch 400 having the shape shown in FIG. 13 or 14 is applied.

Although one embodiment of the present invention has been described above, the concept of the present invention is not limited to the embodiment disclosed herein. Another embodiment may be easily perceived by one of ordinary skill in the art by addition, changing, deleting, adding, and the like a component within an equivalent range of the concept and should be included in the scope of the present invention.

The invention claimed is:

1. A heating patch comprising:
a base substrate having a plate shape and a flexibility;
an electrode portion formed on at least one surface of the base substrate, the electrode portion comprising: a first lead electrode and a second lead electrode arranged along a longitudinal direction and being spaced apart from each other along a width direction of the base substrate, and a first branch electrode extending from the first lead electrode toward the second lead electrode along the width direction, a second branch electrode extending from the second lead electrode toward the first lead electrode along the width direction to be not electrically connected to the first branch electrode and to be disposed adjacent to the first branch electrode over a predetermined portion of a length of the first branch electrode, wherein the first branch electrode and the second branch electrode form a branch electrode pair;
a heating portion comprising a conductive heating material and disposed on the branch electrode pair, wherein the heating portion is configured to create a conductive connection between the first branch electrode and the second branch electrode and generate heat when an electrical power is applied to the first lead electrode and the second lead electrode; and
a cover member disposed on the heating portion to prevent the electrode portion and the heating portion from being exposed externally.

2. The heating patch of claim 1, wherein the base substrate is formed of a nanofiber web of a three-dimensional network structure having micro air holes.

3. The heating patch of claim 1, wherein the first lead electrode has a width greater than those of the first branch electrode and the second branch electrode, and the second lead electrode has a width greater than those of the first branch electrode and the second branch electrode.

4. The heating patch of claim 1, wherein the branch electrode pair comprises: a plurality of branch electrode pairs arranged to be spaced apart along the longitudinal direction of the base substrate, and
wherein a gap between the first branch electrode and the second branch electrode in the branch electrode pair is formed to be smaller than a gap between two adjacent branch electrode pairs.

5. The heating patch of claim 4, wherein the heating portion comprises: a plurality of heating portions disposed on the plurality of branch electrode pairs, respectively, and the plurality of heating portions have a uniform resistance.

6. The heating patch of claim 1, wherein the heating portion has a width equal to or greater than a sum of a width of the first branch electrode, a width of the second branch electrode, and a gap between the first branch electrode and the second branch electrode.

7. The heating patch of claim 1, wherein the conductive heating material is a conductive constant-temperature heating material.

8. The heating patch of claim 1, wherein the cover member is formed of a material having a damp-proof property and elasticity.

9. The heating patch of claim 1, further comprising: an adhesive layer between the heating portion and the cover member.

10. The heating patch of claim 1, wherein the cover member includes: a first part which covers the heating portion; and a second part which extends from the first part to increase a contact area with a user's skin.

11. The heating patch of claim 1, wherein at least a part of the heating patch has irregular widths along the longitudinal direction.

12. The heating patch of claim 1, further comprising a cable protruding externally from the first lead electrode and the second lead electrode for electrical connection with an external power source.

13. The heating patch of claim 1, wherein the cover member includes: a first part covering the heating portion; and a second part extending from the first part, and the second part is connected to a cover member of another neighboring heating patch to form a connection part between two neighboring heating patches.

14. A skin care warming device comprising:

two heating patches according to claim 1; and a pair of connection cables respectively connected to the two heating patches and each including one end connected to another cable, which is connected to an external power source device.

15. A skin care warming device comprising:

two heating patches according to claim 1;

a pair of connection cables respectively connected to the two heating patches;

a connection member which connects the pair of connection cables and has a predetermined length to be worn on a user's body; and a battery electrically connected to the pair of connection cables and embedded in the connection member.

16. The heating patch of claim 1, further comprising: a color-changing layer disposed between the heating portion and the cover member, wherein the color-changing layer includes: a thermo-sensitive color-changing material.

17. The heating patch of claim 1, wherein the base substrate comprises: a thermo-sensitive color-changing material.

\* \* \* \* \*